US00PP14237P29

(12) United States Plant Patent
Bradford

(10) Patent No.: US PP14,237 P2
(45) Date of Patent: Oct. 14, 2003

(54) PLUM TREE NAMED 'YUMMYCRISP'

(50) Latin Name: *Prunus salicina*
Varietal Denomination: 'Yummycrisp'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/300,415

(22) Filed: Nov. 21, 2002

(51) Int. Cl.[7] ..... A01H 5/00
(52) U.S. Cl. ..... Plt./184
(58) Field of Search ..... Plt./184

*Primary Examiner*—Bruce R. Campell
*Assistant Examiner*—Susan B. McCormick

(57) ABSTRACT

The present invention relates to a plum tree, *Prunus salicina*, and more particularly to a new and distinct variety broadly characterized by a large size, vigorous, hardy, heavy blooming, pollen abundant, self-unfruitful, and usually productive tree. The present variety requires cross pollinization from another early blooming plum, such as 'Yummybeaut' (U.S. Plant Pat. No. 13,478). The fruit matures under the ecological conditions described during late July, with first picking on Jul. 25, 2002, but will hang on the tree for nearly thirty more days. The fruit is uniformly medium in size, nearly black in skin color, clingstone in type, yellow with some pink bleeding in flesh color, very firm and crisp in texture, excellent in flavor, and holds well in cold storage for more than thirty days. The present variety was developed from an open pollinated seedling of an unnamed black plum.

1 Drawing Sheet

Botanical classification: *Prunus salicina.*
Variety denomination: 'Yummycrisp'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'Yummycrisp'. Yummy® is a United States Trademark, Ser. No. 75618722, owned by Johnny Appleseed Holdings Limited, Saint Georges Road South RD2, Hastings, New Zealand. Permission to use has been granted to the applicant by contract.

During the spring and summer of 1997, I gathered a mixture of black plums from several different unnamed plum trees. The seeds from that fruit were removed, cracked, stratified, germinated, and grown as seedlings on their own root in my greenhouse. Upon reaching dormancy that year, they were transplanted to a cultivated area of my experimental orchard at Bradford Farms near Le Grand, Calif. in Merced County (San Joaquin Valley). This particular group of seedlings was labeled "Black Plums (OP)". During the fruit evaluation season of 2000, I selected several plum trees that showed excellent characteristics. The present variety was selected as a single tree among the group described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to, 'Friar' (unpatented), by being self-unfruitful and by producing plums that are nearly black in skin color and that first mature in late July, but is distinguished therefrom and an improvement thereon by blooming at least one week earlier, by cross pollinating some other early blooming varieties, such as 'Yummybeaut' (U.S. Plant Pat. No. 13,478), and by producing plums that are smoother in skin surface, that are globose instead of oblate in shape, that acquire more red flesh color at maturity, that are crispier in texture, that are not as large in size, and that hang very firm on the tree much longer.

SUMMARY OF VARIETY

The present plum variety is characterized by a medium size, vigorous, hardy, and usually productive tree. Being self-unfruitful, the present variety requires cross pollinization from another plum that blooms during the early season, such as 'Ambra' (unpatented). The present variety's abundance of blossoms and pollen entices strong bee activity to facilitate pollination and may be utilized as a cross pollinator for some other early blooming commercial varieties, such as 'Yummybeaut' (U.S. Plant Pat. No. 13,478). The fruit matures under the ecological conditions described during late July, with first picking on Jul. 25, 2002, but will hang on the tree for nearly thirty more days. The fruit is uniformly medium in size, nearly black in skin color, clingstone in type, yellow with some pink bleeding in flesh color, very firm and crisp in texture, excellent in flavor, and holds well in cold storage for more than thirty days.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif., and was developed at the state of firm ripe on Aug. 15, 2002, on the original tree during its fifth growing season. All major color code designations are by reference to the Inter-Society Color Council, National Bureau of Standards. Common color names are also used occasionally.

TREE

Size: Medium, reaching and maintaining a height of 11' [3.4 m.] and a spread of 7' [2.1 m.] after five growing seasons utilizing typical dormant pruning.

Vigor: Vigorous, responding typically to irrigation and fertilization. The variety grows about 4' [1.2 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-unfruitful, requiring cross pollination by a suitable early blooming plum, such as 'Yummybeaut' (U.S. Plant pat. No. 13,478).

Bearinq: Usually consistent, but some uncertainty exists if inclement weather is encountered during the blooming period.

Trunk:

*Size.*—Medium, reaching a maximum diameter of 3¼" [83 mm.] after the fifth growing season.

*Texture.*—Shaggy.

*Bark color.*—Grayish brown [61. gy.Br] with Light yellowish brown [76. l.yBr] crevices streaked throughout.

*Lenticels.*—Approximate Number Per Square Inch: 24. Color: Light orange [52. l.O]. Typical Size: ⅛" to ¼" [3.2–6.4 mm.].

Branches:

*Size.*—Diameter of limb is 1¼" [32 mm.] measured 12" above the secondary fork, typical of *Prunus salicina,* and dependent upon cultural practices and climatic conditions.

*Texture.*—Smooth on first year wood, increasing roughness with age.

*Color.*—1st Year Wood Topside: Moderate yellowish brown [77. m.yBr] where exposed to sunlight. 1st Year Wood Underside: Brilliant yellow green [116. brill.YG]. Older Wood: Dark yellowish brown [78. d.yBr].

*Lenticels.*—Number Per Square Inch: More than 100. Color: Dark orange yellow [72. d.OY]. Typical size: 1/64" to ⅛" [0.4–3.2 mm.].

Leaves:

*Size.*—Medium to large. Average Length: 4" [102 mm.]. Average width: 2⅛" [54 mm.].

*Arrangement.*—Alternate.

*Thickness.*—Medium.

*Form.*—Elliptical.

*Apex.*—Acuminate.

*Base.*—Acute with an average angle base angle of 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 9/16" [14.3 mm.]. Average Thickness: 1/16" [1.6 mm.]. Color: Brilliant yellow green [116. brill.YG] with some Dark purplish red [259. d.pR] streaking where exposed to sunlight.

*Stipules.*—Number: 2 per leaf, up to 6 per growing tip. Average Length: ¼" [6.4 mm.]. Color: Strong yellow green [117. s.YG] becoming Dark reddish brown [44. d.rBr] with age.

*Glands.*—Average Number: 2. Position: Both alternate and opposite, positioned at the intersection of the petiole and blade. Size: Small. Form: Globose. Color: Brilliant yellow green [116. brill.YG] becoming Deep reddish brown [41. deep rBr] in the center with age.

*Leaf buds.*—Conic.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Color.*—White [263. White].

Flowers: Perfect, complete, perigynous, usually a single pistil, typically twenty-eight or more stamens, five sepals and petal locations alternately positioned.

*Average flower diameter.*—13/16" [20.6 mm.].

*Number of petals.*—Five, no double blossoms observed.

*Petal shape.*—Oval.

*Petal margin.*—Somewhat wavy.

*Average petal diameter.*—5/16" [7.9 mm.].

*Average petal length.*—⅜" [9.5 mm.].

*Petal apex.*—Rounded.

*Petal base.*—Rounded to somewhat acute.

*Petal color.*—White [263. White].

*Anther color.*—Brilliant orange yellow [67. brill.OY] blending to Light yellow [86. l.Y] toward the center.

*Stigma color.*—Light greenish yellow [101. l.gY].

*Sepal color.*—Brilliant yellow green [116. brill.YG].

*Sepal length.*—5/32" [4 mm.].

*Sepal width.*—⅛" [3 mm.].

*Average pistil length.*—⅜" [9.5 mm.].

*Average stamen length.*—5/16" [7.9 mm.].

*Fragrance.*—Moderate.

*Pollen production.*—Abundant.

*Blooming period.*—Early compared with other varieties, about with 'Ambra' (unpatented).

*Onset of bloom.*—One percent on Feb. 18, 2002.

*Date of full bloom.*—Feb. 28, 2002.

*Duration of bloom.*—One to two weeks, dependent on ambient temperature.

*Number per cluster.*—2 to 7, 3 most frequently.

FRUIT

Maturity when described: Firm ripe, August 15, 2002.

Date of first picking: Jul. 25, 2002.

Date of last picking: Aug. 20, 2002.

Size: Uniform, medium.
*Average diameter axially.*—2⅜" [60.3 mm.].
*Average diameter across suture plane.*—2 5/16" [58.7 mm.].
*Typical weight.*—4.6 ounces [130 grams].
Form: Uniform, symmetrical, globose to slightly oblong.
*Longitudinal section form.*—Oval.
*Transverse section through diameter.*—Circular.
Suture: A shallow groove extending from the base to the apex with a slight depression at the pistil point.
Ventral surface: Rounded, slightly lipped throughout.
Lips: Slightly unequal.
Cavity: Flaring, circular, suture showing on one side.
*Depth.*—7/16" [11.1 mm.].
*Breadth.*—15/16" [23.8 mm.].
Base: Truncate, but slightly cuneate when viewed along the suture.
Apex: Rounded with a small hump just beyond the pistil point.
Pistil point: An inconspicuous Light yellowish brown [76. l.yBr] dot.
Stem: Medium.
*Average length.*—⅜" [9.5 mm.].
*Average width.*—3/32" [2.4 mm.].
Skin:
*Thickness.*—Medium.
*Surface.*—Smooth.
*Tenacity.*—Tenacious to flesh.
*Astringency.*—Slight.
*Tendency to crack.*—None observed.
*Color.*—Reddish black [24. rBlack] smoothly blending to Very dark red [17. v.d.R] with Strong reddish brown [40. s.rBr] stem markings typical and Light orange yellow [70. l.OY] freckling throughtout.
*Bloom.*—Abundant.
Flesh:
*Color.*—Pale orange yellow [73. p.OY] with Moderate red [15. m.R] streaking toward the stone and skin.
*Surface of pit cavity.*—Covered with short Deep pink [3. deep Pk] fibers that tear from the stone when strongly twisted.
*Amygdalin.*—Moderate.
*Juice.*—Abundant, rich.
*Texture.*—Extremely firm and crisp, will hang 30 days on tree.
*Fibers.*—Abundant, fine.
*Ripens.*—Fairly even.
*Flavor.*—A blend of mild acid and very high sugar, typically 20 to 24 brix.
*Aroma.*—Slight.
*Eating quality.*—Excellent.

STONE

Type: Clingstone.
Form: Oval.
Hilum: Narrow.
Base: Rounded.
Apex: Rounded with a very sharp tip 1/16" [1.6 mm.] in length.
Sides: Equal.
Surface: Rough with no pitting or grooves.
External color of stone: Moderate orange yellow [71. m.OY].
Pit wall color when cracked: Light yellowish brown [76. l.yBr].
Cavity surface color: Deep yellowish brown [75. deep yBr].
Average pit wall thickness: 5/64" [2.0 mm.].
Average width: 13/16" [20.6 mm.].
Average length: 1 1/16" [27.0 mm.].
Average breadth: 7/16" [11.1 mm.].
Tendency to split: None observed in dry season.
Kernel:
*Form.*—Oval.
*Skin color.*—Moderate yellow [87. m.Y].
*Pellicle color.*—Dark yellowish brown [78. d.yBr].
*Vein color.*—Dark yellowish brown [78. d.yBr].
*Taste.*—Bitter.
*Viable.*—Yes.
*Average width.*—½" [12.7 mm.].
*Average length.*—⅝" [15.9 mm.].
*Amygdalin.*—Abundant.

USE

Market: Fresh market and long distance shipping.
Keeping quality: Excellent. Fruit quality observed to remain in good condition in after 30 days in standard cold room at 36° Fahrenheit [2° Celsius].
Shippinq quality: Excellent.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'Friar' (unpatented), by being self-unfruitful and by producing plums that are nearly black in skin color and that first mature in late July, but is distinguished therefrom and an improvement thereon by blooming at least one week earlier, by cross pollinating some other early blooming varieties, such as 'Yummybeaut' (U.S. Plant Pat. No. 13,478), and by producing plums that are smoother in skin surface, that are globose instead of oblate in shape, that acquire more red flesh color at maturity, that are crispier in texture, that are not as large in size, and that hang very firm on the tree much longer.

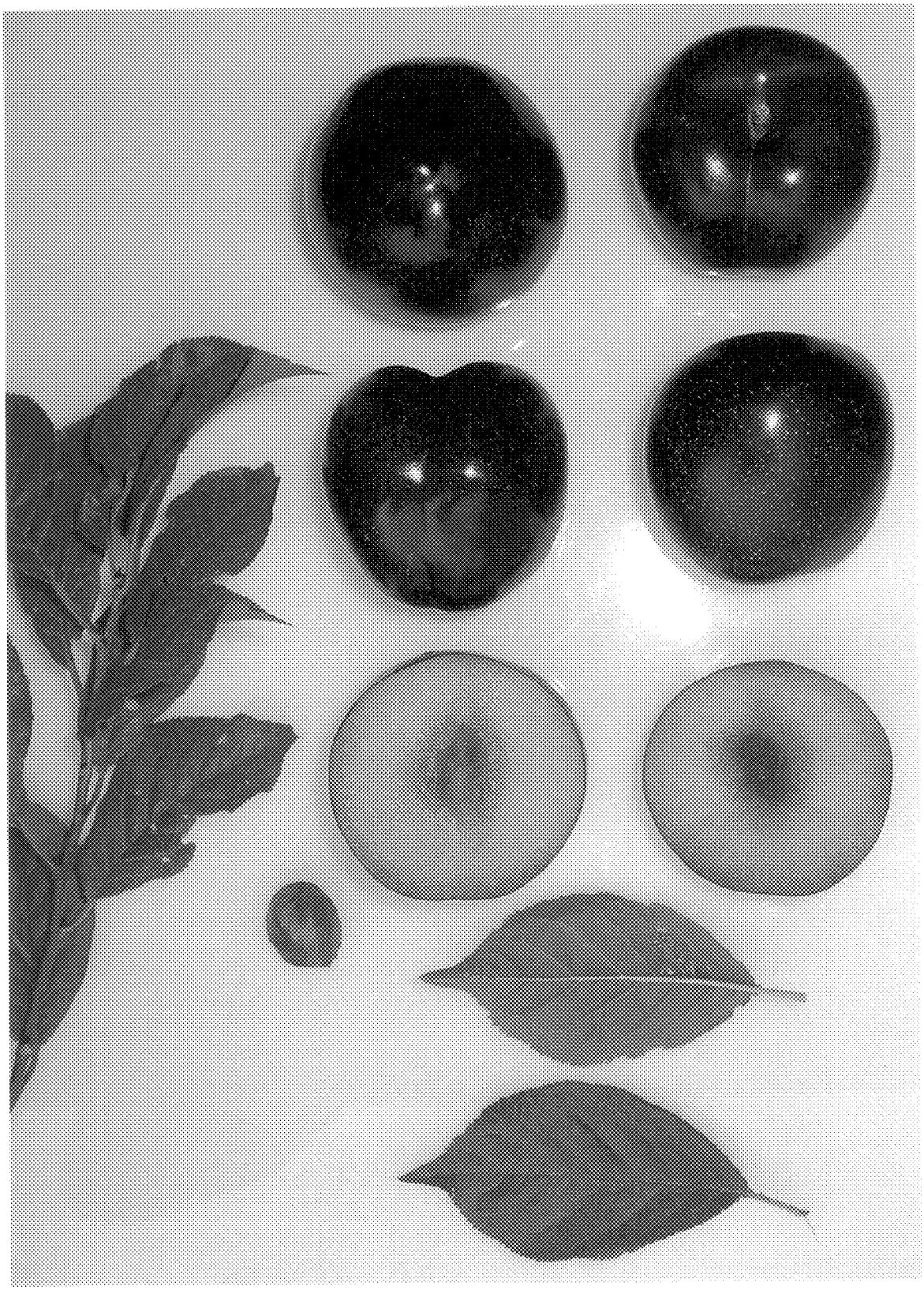

* * * * *